United States Patent [19]

Rao

[11] Patent Number: 5,481,051
[45] Date of Patent: Jan. 2, 1996

[54] 2,2-DICHLOROHEXAFLUOROPROPANE HYDROGENOLYSIS

[75] Inventor: V. N. Mallikarjuna Rao, Wilmington, Del.

[73] Assignee: E. I. Du Pont de Nemours and Company, Wilmington, Del.

[21] Appl. No.: 351,927

[22] Filed: Dec. 8, 1994

[51] Int. Cl.$^6$ .................................................... C07K 19/08
[52] U.S. Cl. .................................................... 570/176
[58] Field of Search ........................................ 570/176

[56] References Cited

U.S. PATENT DOCUMENTS

| | | | |
|---|---|---|---|
| 2,942,036 | 6/1960 | Smith et al. | 260/653 |
| 4,319,060 | 3/1982 | Cunningham | 570/177 |
| 4,873,381 | 10/1989 | Keliner et al. | 570/176 |
| 5,036,036 | 6/1991 | Lerou | 502/317 |
| 5,091,600 | 2/1992 | Moore et al. | 570/151 |
| 5,171,901 | 12/1992 | Gassen et al. | 570/168 |

FOREIGN PATENT DOCUMENTS

| | | |
|---|---|---|
| 1-319441 | 12/1989 | Japan . |
| 1578933 | 11/1980 | United Kingdom . |
| WO94/20440 | 9/1994 | WIPO . |

OTHER PUBLICATIONS

Bitner, J. L. et al, "Thermochemical and Photochemical studies on organic fluorine compounds", *Chemical Abstracts*, 54:22311C (1962).

Bitner, J. L. et al, *U.S. Dept. of Comm. Off. Tech. Serv./ Report 136732*, pp. 25–27 (1958).

Zubovich, I. A., "Oxidation—Reduction Catalysis by Palladium–Gold and Palladium—Silber Systems on Different Types of Carrier", *Russian Journal of Phys. Chem.*, 56(5), 798–799 (1982).

Sokolskii, D. V. et al, "Liquid–phase Hydrogenation of β–Ionone on a Stationary Ni–Cr$_2$O$_3$ Catalyst in a Flow Apparatus under Hydrogen Pressure", *Russian Journal of Phys. Chem.*, 56(7), 1075–1076 (1982).

*Primary Examiner*—Alan Siegel

[57] ABSTRACT

A process is disclosed for the monohydrogenolysis of 2,2-dichlorohexafluoropropane to 2-chloro-2-hydrohexafluoropropane. The process involves reacting the 2,2-dichlorohexafluoropropane with hydrogen at an elevated temperature of about 150° C. or less in the presence of a catalyst containing a catalytically effective amount of palladium supported on trivalent chromium oxide in the presence of an acid of the formula HZ (where Z is Cl and/or F) to produce 2-chloro-2-hydrohexafluoropropane with a selectivity of over 70% based upon the 2,2-dichlorohexafluoropropane converted.

1 Claim, No Drawings

2,2-DICHLOROHEXAFLUOROPROPANE HYDROGENOLYSIS

FIELD OF INVENTION

This invention relates to catalytic hydrogenolysis of halofluorocarbons, and more particularly to the hydrogenolysis reactions of 2,2-dichlorohexafluoropropane using palladium-containing catalysts.

BACKGROUND

Various processes for the catalytic hydrogenolysis of chlorofluorocarbons and hydrochlorofluorocarbons are known. For example, British Patent Specification 1,578,933 illustrates that mixtures of $C_2Cl_2F_4$ isomers can be subjected to hydrogenolysis over a particulate catalyst of palladium on charcoal (which was intimately mixed with glass helices to prevent clogging) or palladium on alumina, to mixtures of $C_2H_2F_4$. U.S. Pat. No. 2,942,036 discloses the reaction of 1,2,2-trichloropentafluoropropane with hydrogen in the presence of palladium on activated carbon catalyst to produce 1,2,2-trihydropentafluoropropane. The examples show that under the conditions of the experiments one of the products from this reaction is $CF_3CH=CF_2$. The carbon support may be treated prior to depositing palladium on the support with aqueous HF for the purpose of removing silica from the carbon. Japanese Patent Application Publication Hei 1(1989)-319441 discloses a process where one chlorine atom is selectively replaced by hydrogen in 1,1,1-trichlorotrifluoroethane using a platinum catalyst. For comparison, a palladium on carbon catalyst is disclosed to produce 1,1,1-trifluoroethane as the major product under the conditions of the experiment.

It is well known that the hydrogenolysis of compounds such as chlorofluorocarbons to replace chlorine by hydrogen produces hydrogen chloride as a co-product and that loss of fluorine (e.g., to produce overhydrogenated products) can produce HF as a by-product.

SUMMARY OF THE INVENTION

The present invention provides a process for the monohydrogenolysis of 2,2-dichlorohexafluoropropane (i.e., $CF_3CCl_2CF_3$, or CFC-216aa) to 2-chloro-2-hydrohexafluoropropane (i.e., $CF_3CHClCF_3$, or HCFC-226da). The process comprises reacting said 2,2-dichlorohexafluoropropane with hydrogen at an elevated temperature of about 150° C. or less in the presence of a catalyst containing a catalytically effective amount of palladium supported on trivalent chromium oxide in the presence of an acid of the formula HZ, where Z is selected from the group consisting of Cl, F and mixtures thereof, to produce 2-chloro-2-hydrohexafluoropropane with a selectivity of over 70% based upon the 2,2-dichlorohexafluoropropane converted.

DETAILED DESCRIPTION

The catalysts suitable for the process of this invention comprise palladium and may optionally contain other components such as other Group VIII metals. The palladium is supported on chromium oxide. Any source of chromium oxide is suitable, but chromium oxide prepared by the thermal decomposition of $(NH_4)_2Cr_2O_7$ is especially preferred. A procedure for the preparation of $Cr_2O_3$ by the thermal decomposition of $(NH_4)_2Cr_2O_7$ is disclosed in U.S. Pat. No. 5,036,036, the entire contents of which are incorporated herein by reference.

The acid HZ is at least partially produced during the reaction as the halogen Cl is removed from the starting material as a result of the hydrogenolysis. Accordingly, Z is ordinarily at least in part Cl. Also of note are embodiments where Z is partially F (i.e., the acid is a mixture of HCl and HF). HF can be present for example, as a result of overhydrogenolysis, wherein fluorine substituents of the starting material are partially replaced by hydrogen. HF can also be present in the reaction feed. For example, residual HF can be present from processes used to make the 2,2-dichlorohexafluoropropane. Of note in this regard are embodiments where said starting material is a component of an azeotrope of HF and said starting material, and starting material from said azeotrope is reacted with hydrogen in the presence of HF from said azeotrope.

Unlike alumina supports which are readily fluorinated, chromia fluorinates much more slowly under the same reaction conditions. Without wishing to be bound by theory, it is believed that because of the slower fluorination, chromia supports maintain their surface area longer than alumina supports; thereby enhancing catalyst life.

The palladium-containing material used to prepare the catalyst is preferably from a palladium salt (e.g., palladium chloride). The other metals which may be added to the catalyst include those from Group VIII (e.g., Pt, Rh, Ru or Ni). The metal may be added in the conventional manner (e.g., as a soluble salt of the metal). The concentration of palladium supported on the chromium oxide support is typically within the range from about 0.2% to about 5% by weight of the catalyst. The concentration of other Group VIII metals, when present, is typically within the range of from 0% to about 3% by weight of the catalyst, but palladium is ordinarily at least 60% by weight of the total supported metal, (preferably, at least 80% of the total supported metal).

The hydrogenolysis of the present invention is conducted at an elevated temperature. Ordinarily the temperature is about 150° C. or less. Typically satisfactory reaction rates are achieved at operating temperatures of about 100° to 125° C. Generally, in order to provide substantial hydrogenolysis product yields, the amount of hydrogen used is at least about 0.5 mole per mole of the organic starting material. To provide yields desired in many embodiments, at least stoichiometric amounts of hydrogen are used. A considerable excess of hydrogen can also be advantageously employed to provide the yields desired in many embodiments in addition to serving as a heat sink to reduce the overall temperature rise in the reactor. The amount of the monohydrogenolysis product in the reaction product mixture containing the same number of fluorines as the starting material is typically at least 70%.

The process of this invention is especially suitable for the production of 2-chloro-2-hydrohexafluoropropane (HCFC-226da) from 2,2-dichlorohexafluoropropane (CFC-216aa). The monohydrogenolysis product, HCFC-226da is a valuable intermediate for the synthesis of other fluorine containing materials, such as $CF_3CHFCF_3$ (HFC-227ea) which is useful as a fire extinguishant.

The reaction products may be separated by conventional techniques, such as distillation. Hydrochlorofluorocarbons such as 2-chloro-2-hydrohexafluoropropane (HCFC-226da) likely form azeotropes with HF; and conventional decantation/distillation may be employed if further purification of HCFC-226da is desired.

Pressure is not critical. Atmospheric and superatmospheric pressures are the most convenient and are therefore preferred.

Practice of the invention will become further apparent from the following non-limiting examples.

EXAMPLE $CF_3CCl_2CF_3 \rightarrow CF_3CHClCF_3$

Catalyst Preparation

A solution containing palladium chloride (2.88 g), conc. hydrochloric acid (3 mL) and deionized water (100 mL) was prepared in a round-bottom flask. To this solution was added chromium oxide, $Cr_2O_3$, (98 g, 10×20 mesh (1.7×0.83 mm)) prepared by the pyrolysis of $(NH_4)_2Cr_2O_7$. The resulting slurry was stirred frequently and then dried in air at 150° C. for about 18 hours; followed by calcination in air for about 8 hours. Palladium on chromium oxide (96.7 g), containing about 2% palladium was isolated.

Hydrogenolysis of CFC-216aa Using Palladium on Chromium Oxide Catalyst

Liquid CFC-216aa ($CF_3CCl_2CF_3$), 3 mL/hour was vaporized and mixed with 20 cc/minute of hydrogen. This vapor mixture was sent through a 0.5" (1.3 mm) O.D.×8" (203 mm) Hastelloy™ nickel alloy reactor containing 19.2 g of 10×20 mesh (1.7 mm×0.83 mm) palladium on chromium oxide catalyst (2 weight percent palladium) heated in a fluidized sand bath maintained at 100° C. The catalyst was heated at 400° C. in a stream of hydrogen fluoride for about 30 minutes and subsequently reduced in a stream of hydrogen at about 150° C. for about two hours prior to use (at 100° C.) for the hydrogenolysis. Organic product analysis using conventional gas chromatography after the catalyst was in use for about twenty hours of operation showed that CFC-216aa conversion was about 92%. The hydrogen-containing products included 4.0% HFC-236fa ($CF_3CH_2CF_3$), 86.0% HCFC-226da ($CF_3CHClCF_3$) and small amounts of other products. Only a small portion of the total reactor effluent was sent to the gas chromatograph for organic product analysis. The bulk of the product stream which also contains inorganic acids such as HCl and HF was sent to a caustic scrubber for neutralization of the acids.

The above reaction was repeated except that the reaction temperature was 150° C. CFC-216aa conversion was essentially complete. The hydrogen-containing products included about 9.5% HFC-236fa and 83% HCFC-226da and small amounts of other products.

The above reaction was repeated except that the reaction temperature was 200° C. Again, CFC-216aa conversion was essentially complete. In addition to the hydrogen-containing products, HFC-236fa (23%) and HCFC-226da (62%), there was about 10% propane in addition to other minor by-products.

COMPARATIVE EXAMPLE

Hydrogenolysis of CFC-216aa Using Palladium on Low-Ash Acid-Washed Carbon

Carbon Support

The carbon support used in the examples was a 4×8 mesh (about 4.7 mm×2.4 mm) commercial grade coconut shell carbon which had (before washing) an ash content of about 2.6 weight percent. After hydrochloric acid washing, the carbon support had an ash content of less than about 0.1 weight percent.

Liquid CFC-216aa, 3 mL/hour, was vaporized and mixed with 10 cc/minute of hydrogen. This vapor mixture was sent through a 0.5" (12.7 mm) O.D.×8" (203 mm) Hastelloy™ nickel alloy reactor containing 7.2 g of 0.5 weight percent palladium supported on acid-washed carbon maintained at 150° C. using a fluidized sand bath. Only a small portion of the total reactor effluent was sent to the gas chromatograph for organic product analysis. The bulk of the product stream which also contains inorganic acids such as HCl and HF was sent to a caustic scrubber for neutralization of the acids. Organic product analysis using conventional gas chromatography indicated that about 90% of the starting material had been converted. The hydrogen-containing products included 15.7% 2,2-dihydrohexafluoropropane (HFC-236fa), 54.3% 2-chloro-2-hydrohexafluoropropane (HCFC-226da), 12.3% 2-hydropentafluoropropene, and 1.7% 1,2,2-trihydropentafluoropropane (HFC-235fa) and small quantities of other compounds.

This example was repeated except that the hydrogen flowrate was increased to 30 cc/minute. Organic product analysis using conventional gas chromatography indicated that the starting material conversion was essentially complete. The hydrogen-containing products included 24.8% 2,2-dihydrohexafluoropropane (HFC-236fa), 54.6% 2-chloro-2-hydrohexafluoropropane (HCFC-226da) and 19.8% 1,2,2-trihydropentafluoropropane (HFC-235fa) and small quantities of other compounds.

This comparative experiment illustrates that when using palladium supported on acid-washed carbon as catalyst for the hydrogenolysis of CFC-216aa (where two chlorines of the starting compound are on the middle carbon and the two adjacent carbons contain trifluoromethyl groups) an olefin and/or a saturated product containing one less fluorine than the starting compound can be produced in significant amounts.

What is claimed is:

1. A process for the monohydrogenolysis of 2,2-dichlorohexafluoropropane to 2-chloro-2-hydrohexafluoropropane, comprising:

reacting said 2,2-dichlorohexafluoropropane with hydrogen at an elevated temperature of about 150° C. or less in the presence of a catalyst containing a catalytically effective amount of palladium supported on trivalent chromium oxide in the presence of an acid of the formula HZ, where Z is selected from the group consisting of Cl, F and mixtures thereof, to produce 2-chloro-2-hydrohexafluoropropane with a selectivity of over 70% based upon the 2,2-dichlorohexafluoropropane converted.

* * * * *